United States Patent [19]

Dorsey et al.

[11] Patent Number: 5,217,024
[45] Date of Patent: Jun. 8, 1993

[54] TISSUE SAMPLING DEVICE WITH VISUAL AND TACTILE INDICATOR

[76] Inventors: Denis P. Dorsey, 51 Rainlily Rd., Levittown, Pa. 19056; James D. Dorsey, 417 Glendale Rd., Wilbraham, Mass. 01095

[21] Appl. No.: 858,893
[22] Filed: Mar. 27, 1992
[51] Int. Cl.⁵ ............................................. A61B 10/00
[52] U.S. Cl. ................................... 128/758; 128/749; 128/757; 606/160
[58] Field of Search ............... 128/757, 758, 759, 754, 128/753, 757, 751, 750, 749; 604/275, 276, 117; 606/159, 160, 161

[56] References Cited

U.S. PATENT DOCUMENTS

| | | | |
|---|---|---|---|
| 2,715,899 | 8/1955 | MacLean | 128/758 |
| 3,438,366 | 4/1969 | Kariher et al. | 128/757 |
| 3,796,211 | 3/1974 | Kohl | 128/757 |
| 4,384,587 | 5/1983 | Milgrom | 128/757 |
| 4,396,022 | 8/1983 | Marx | 128/758 |
| 4,777,947 | 10/1988 | Zwick | 128/757 |

*Primary Examiner*—Max Hindenburg
*Assistant Examiner*—Guy V. Tucker
*Attorney, Agent, or Firm*—Dennison, Meserole, Pollack & Scheiner

[57] ABSTRACT

A medical device for removing tissue from a body cavity includes a tubular shaped handle securely connected and in communication with an elongated hollow tubular probe. The probe includes a spherical tip and an open area with a notch. The open area includes a cutting edge for removing tissue. The handle has a visual and tactile indicator in the general shape of a raised arrow. The raised indicator is axially aligned with open area of the probe. Accordingly, the user can feel or see the raised indicator and know the exact orientation of the open area when the cutting edge of the device is in the body cavity.

9 Claims, 1 Drawing Sheet

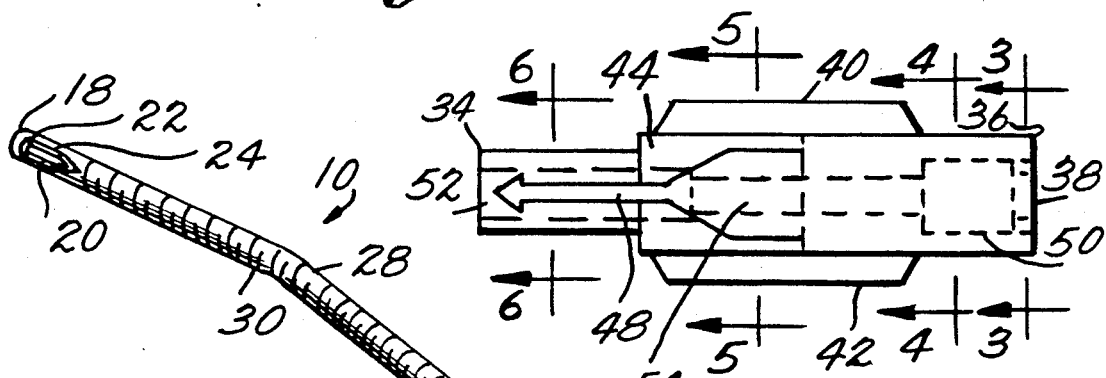
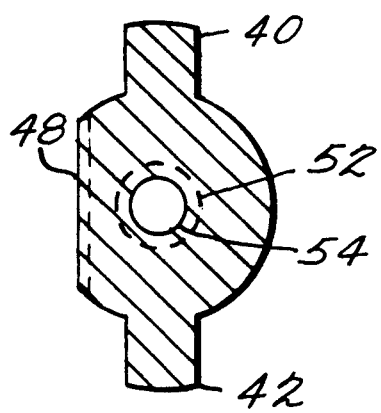
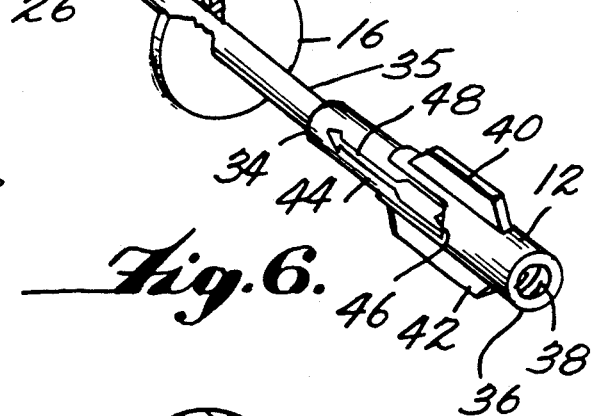
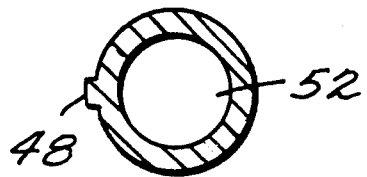
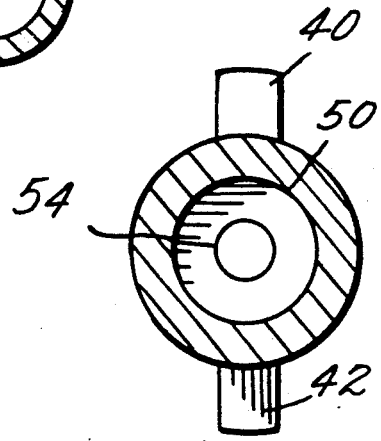

TISSUE SAMPLING DEVICE WITH VISUAL AND TACTILE INDICATOR

BACKGROUND OF THE INVENTION

1. Field of the Invention

The invention relates to a medical device having a visual and tactile indicator for collecting tissue samples from bodily cavities, such as the human uterus.

2. Discussion of Prior Art

Heretofore, endometrial tissue sampling devices for securing and removing endometrial tissue terminated at the distal end with a scraping member. At the proximal end, a handle member is attached to a syringe or pump to provide a sucking action to collect the tissue sample. The handle member of the prior art is difficult to manipulate by the user. Additionally, the user has no idea where the scraping tip is located in the body cavity and this awkward and clumsy scraping technique causes pain and discomfort to the patient.

In U.S. Pat. No. 3,777,643 to Binard et al, the endometrial sampler comprises a rigid hollow tube having a sampling end with a plurality of sampling ports communicating with the interior of the tube. The probe does not have a cutting port. Basically, the sampler is a flexible plastic rod with a stainless steel probe that is manipulated with a syringe to gather fluid samples from the uterus.

In U.S. Pat. No. 4,340,066 to Shah, the instrument includes a longitudinal chamber having a slot and a transverse slot. The handle is connected to a syringe and the user awkwardly and blindly scrapes with the entire probe to gather tissue sample.

U.S. Pat. No. 4,393,879 to Milgrom discloses a curette with a tissue-scraping spoon or the like at one end thereof. The handle member is operated by utilizing both hands to produce a sucking action to collect the tissue samples.

In U.S. Pat. No. 4,396,022 to Marx, an endometrial tissue sampling apparatus includes a probe made of stainless steel for scraping and removing endometrial tissue. The probe is covered in a sheath. The user inserts the probe into the endometrial cavity and begins blindly scraping and cutting tissue samples. A syringe is attached to the sheath and utilized to create a vacuum so the tissue samples can be sucked into the shaft and then into the syringe. The device does include an arrow on the handle to visually signal orientation for insertion. However, once the handle is removed to insert the syringe, the orientation of the cutting edge is lost to the user. Accordingly, the user begins to awkwardly and blindly scrape for tissue samples.

U.S. Pat. No. 4,627,444 to Booker is a device for sampling tissues and fluids from body cavities. This device has a tube within a tube, with a retrieval line, multiple cutting edges, a protective sleeve, a stop sleeve, a plug and a cap. The catheter has integral parts and appears to be a rather difficult instrument to use. After insertion, the protective cap or tip is dislodged into the patient and the probe or curette includes a plurality of notches for blindly scraping tissue samples from the cavity walls. A syringe is attached and provides suction to collect the scraped tissue samples.

The tissue sampling devices exemplified in the patents referred to hereinabove illustrate the many improvements made over the years for retrieving endometrial tissue samples. There still exists, however, in this industry, a need for a medical device for collecting tissue samples which allows the user or doctor to control the distal cutting edge in a manner that particularly improves the safety, efficiency and economy of the device, and to simplify operation and maneuverability of the scraping element.

SUMMARY OF THE INVENTION

The present invention includes a clearly visible and tactile indicator that allows a doctor or user to know exactly how the cutting edge or scraper is oriented within the body cavity at all times. The indicator is in the shape of a raised arrow on a lower part of the device and the indicator is aligned such that when the instrument is inserted into the body cavity, the hidden cutting edge or scraper is precisely oriented with the raised arrow. This indicator is clearly identifiable by the user either visually or by touch.

The curette of the present invention has a centimeter scale embossed on the probe portion that provides means measuring the depth of insertion thereby eliminating the necessity of removing the probe and using an external ruler to accomplish this task.

The device of the present invention includes a large diameter disk or stopette that moves easily up the probe from the cutting edge to the handle but will not move easily from the handle to the cutting edge. This stopette enhances the accurate measuring of the depth or penetration and, more importantly, the stopette is large enough in diameter and especially designed to move unidirectional so as to not get lost within the patient.

Accordingly, it is an object of the invention to provide a medical device for removing tissue from a body cavity.

Another object is to provide a handle being tubular shaped and having a proximal end with a female threaded portion for receiving other medical devices with male threaded portions, wherein the threaded portions provide an airtight seal.

An object of the invention is to have a plurality of finger tabs protruding outwardly from the tubular shaped handle, and positioned between the distal and proximal ends.

A further object is to have a cut away portion positioned near the middle of the tubular shaped handle and between the plurality of finger tabs and extending to the distal end, wherein the cut-away portion expands near the distal end such that the outer diameter of the tubular shaped handle near the distal end is less than the outer diameter of the tubular handle near the proximal end.

An additional object of the invention is to provide a raised indicator means covering a part of the cut-away portion and extending nearly to the distal end of the tubular handle, wherein the raised indicator is positioned between the plurality of finger tabs.

An advantage of the invention is an elongated hollow tubular member having distal and proximal ends, wherein the proximal end is securely connected to the distal end of the tubular handle.

Another advantage is that the distal end of the elongated hollow tubular member has a spherical tip and an opening area with a notch.

A further advantage of the invention is that the open area is positioned on the elongated hollow tubular member so as to be aligned with the raised indictor means on the handle and a user merely needs to feel or see the raised indicator for determining the position of the open area;

Another object of the invention is to provide a slight bend area on the tubular member positioned between the distal tip and the tubular handle for facilitating entrance into the body cavity.

A further object of the invention is to provide a scale embossed on the tubular member for providing visual measurements of penetration into the body cavity.

An advantage of the invention is that the proximal end of the handle member further includes a female threaded portion for receiving male threaded medical devices.

An additional advantage of the invention is that the hollow tubular member further includes a slight bend area positioned between the distal tip and the handle member for facilitating entrance of the device into the body cavity.

Further objects and advantages of the invention will become apparent from a consideration of the drawings and ensuing description thereof.

BRIEF DESCRIPTION OF THE DRAWINGS

FIG. 1 is an enlarged prospective view of a medical device made according to the present invention;

FIG. 2 is an enlarged view of the handle member of the present invention;

FIG. 3 is an enlarged cross sectional view taken on line 3—3 in FIG. 2;

FIG. 4 is an enlarged cross sectional view taken on line 4—4 in FIG. 2;

FIG. 5 is an enlarged cross sectional view taken on line 5—5 in FIG. 2; and

FIG. 6 is an enlarged cross sectional view taken on line 6—6 in FIG. 2.

DESCRIPTION OF THE INVENTION

A tissue sampling device with a visual and tactical indicator for collecting body tissue is shown in FIG. 1 and generally indicated by reference numeral 10. The tissue sampling device includes a handle member 12. The handle 12 is connected to a probe 14. The probe 14 includes a readily detachable stopette 16.

The probe 14 includes a distal tip 18. The distal tip is spherical or round at its outer end for patient comfort when inserted into the endometrial cavity of a female patient. Adjacent the distal tip 18 is an opening 20. The opening 20 includes a notch 22 and a cutting edge 24. The cutting edge 24 extends around the perimeter of the opening 20. The notch or scraper 22 together with the cutting edge 24 of opening 20 are utilized to provide scraping action to loosen or cut tissue from the body cavity wall. The probe 14 is generally tubular or cylindrical shape having a hollow storage chamber 26 for receiving tissue samples scraped or cut and collected through opening 20. The probe 14 includes a lateral obtuse angle defining a bend 28. The bend 28 enhances the entrance of the probe into the uterus.

The probe 14 also includes a scale 30 embossed on the probe beginning adjacent the opening 20 and extending nearly the length of the probe 14.

The stopette 16 is a radial circular disk shaped flange. The stopette 16 is readily attachable to the probe and is somewhat large in diameter. The stopette 16 is unidirectional and slides in the direction of handle member 12, but is prohibited from readily moving toward the opening 20 because of grippers 32. The large size of the stopette 16 is especially designed so as not to get lost within the patient. The stopette 16 is utilized to ensure the depth of the insertion, as measured along scale 30, is accurate and precise.

Handle member 12 includes a distal end 34. The distal end 34 receives the probe proximal end 35. A secure bond engages the two members and secures the ends 34 and 35 together to operate as one tissue sampling device 10. The proximal end 36 of handle member 12 includes an inner threaded female portion 38 to receive a syringe or pump member to provide suction as is commonly known in the art.

The handle member 12 further includes a pair of fin shaped finger tabs 40, 42. Fin shaped finger tabs 40, 42 are axially aligned on the tubular handle member 12 and extend perpendicular from the handle member 12. The fin shaped finger tabs 40, 42 facilitate the attaching of the handle member to a syringe or pump. The tabs 40, 42 allow the user to provide enough force or holding power to attach the handle member to a further medical device in order to connect the devices for a good seal and an airtight fit. The fin shaped finger tabs 40, 42 are positioned or centered nearly in the middle of the handle member 12.

Approximately a third of the way from the distal end 34, the handle member reduces in outer diameter and recesses along top 44 of the handle member 12 to approximately a center point 46 to form a cut away portion. Extending from the center 46 and the cut away portion of the handle member 12 is a raised combined tactile and visual means 48 in the nature of a forwarding directed arrow with a height less than the recessed area. The indicator 48 is positioned between the fin shaped finger tabs 40, 42 and axially aligned with the probe 14 such that opening 20 is oriented and aligned with raised arrow indicator 48.

This combined tactile and visual means indicator 48 permits the doctor or user to know exactly where the cutting edge 24 is oriented within the body cavity at all times. The indicator 48 is a raised arrow and it is aligned such that when the instrument is inserted into the body the hidden cutting edge 24 is precisely oriented with the arrow indicator 48. Because of the alignment, position and shape, the indicator 48 is clearly identifiable either visually or by touch.

Referring now to FIGS. 2 through 6, the inner elements of handle member 12 will now be discussed.

Handle member 12 includes three different sized diameter cavities or chambers. At the proximal end 36 is the inner female threaded portion 38. The inner female threaded portion 36 receives a syringe or pump which extends into the first cavity or chamber 50.

At the distal end 34 of handle member 12 is a second cavity or chamber 52. Chamber 52 is large enough to receive probe 14 such that probe 14 slips into the handle member 12 and is securely bonded therein. In this position, the raised arrow 48 is axially aligned with opening 20.

In the center of handle member 12 is a third chamber or cavity 54. This cavity or chamber 54 has the same diameter as probe chamber 26. Each of these chambers 50, 52 and 54 are axially aligned so when the tissue sampling device 10 is connected to a syringe or a pump, opening 20 can communicate the entire length of the probe 14 and through the handle member 12.

While the above description contains many specificities, these should not be construed as limitations on the scope of the invention, but rather as exemplification of one preferred embodiment thereof. Many other variations are possible. For example, the handle member can be color-coded with international color-codes. The 3mm tissue sampling device can be color coded orange, the 4mm is color coded yellow and the 5mm can be color coded green. These color codes aid the selecting of the proper diameter probe for retrieving body tissues. Accordingly, the scope of the invention should be determined not by the embodiment illustrated, but by the appended claims and their legal equivalents.

We claim:

1. A medical device for sampling tissue from a body cavity, said device comprising:
   a tubular shaped handle member, said handle member including:
   a top portion;
   a proximal end for receiving other medical devices and providing an airtight seal;
   a distal end;
   a distal portion; a proximal portion;
   a middle portion connecting said proximal and distal portions;
   a plurality of finger tabs protruding outwardly from said tubular shaped handle, and positioned in said middle portion, said plurality of finger tabs providing gripping means;
   a cut away portion positioned on said top and distal portions, said cut away portion on said top and distal portions of said tubular shaped handle, said cut away portion on said top portion distal between said plurality of finger tabs, and from a point in said middle portion to said distal portions of said tubular shaped handle, said cut away portion on said distal portions extending radially around said distal portion so an outer diameter of said tubular shaped handle at said distal portion is less than an outer diameter of said tubular handle at said proximal portion;
   raised indicator means covering part of said cut away portion and extending outwardly from said top portion of said tubular handle means and said distal portion of said tubular handle, said raised indicator means being positioned between said plurality of finger tabs, and said raised indicator means providing visual orientation of the medical device and providing tactile orientation of the medical device;
   an elongated hollow tubular member having distal and proximal ends, said proximal end being securely connected to said distal end of said tubular handle, said distal end having a spherical tip and an open area with a notch near said tip, said open area including means for facilitating the sampling of tissue, said open area positioned on said elongated hollow tubular member and aligned with said raised indicator means on said handle.

2. The medical device for sampling tissue from a body cavity, as recited in claim 1, wherein said proximal end of said handle member further includes a female threaded portion for receiving male threaded medical device.

3. The medical device for sampling tissue from a body cavity as recited in claim 1, wherein said hollow tubular member further includes a slight bend area positioned between said distal tip and said handle member for facilitating entrance of said device into the body cavity.

4. The medical device for sampling tissue from a body cavity as recited in claim 3, wherein said hollow tubular member further includes a scale embossed on said tubular member for providing visual measurements of penetration into the body cavity.

5. A medical device for surgically removing tissue from a body cavity for sampling the tissue, said medical device comprising;
   a hollow tubular shaped handle having an inner and outer diameter, said handle including a proximal end for receiving other medical devices, and a distal end;
   an elongated hollow tubular probe having distal and proximal ends, said probe proximal end securely connected to said handle distal end, said probe distal end having a spherical tip and an open area near said tip, said open area including a cutting edge for surgically removing tissue from the body cavity;
   said hollow tubular shaped handle including a top portion, a proximal portion, a distal portion, and a middle portion connecting said proximal and distal portions;
   a plurality of finger tabs extending outwardly from said middle portion;
   a cut away portion positioned on said top and distal portions of said tubular shaped handle, said cut away portion on said top portion extends between said plurality of finger tabs, and from a point in said middle portion to said distal portion of said tubular shaped handle, said cut away portion on said distal portion extending radially around said distal portion so an outer diameter of said tubular shaped handle at said distal portion is less than an outer diameter of said tubular handle at said proximal portion;
   raised indicator means covering part of said cut away portion and extending outwardly from said top portion of said tubular handle means and said distal portion of said tubular handle, said raised indicator means being positioned between said plurality of finger tabs, and said raised indicator means providing visual orientation of the medical device and providing tactile orientation of the medical device.

6. The medical device for sampling tissue from a body cavity, as recited in claim 5, wherein said proximal end of said handle member further includes a female threaded portion for receiving male threaded medical devices.

7. The medical device for sampling tissue from a body cavity as recited in claim 5, wherein said hollow tubular member further includes a slight bend area positioned between said distal tip and said handle member for facilitating entrance of said device into the body cavity.

8. The medical device for sampling tissue from a body cavity as recited in claim 7, wherein said hollow tubular member further includes a scale embossed on said tubular member for providing visual measurements of penetration into the body cavity.

9. The medical device for sampling tissue from a body cavity as recited in claim 7, wherein said device further includes unidirectional stop means for detachably connecting to said probe, said stop means having means for gripping said probe, and said gripping means preventing movement of said stop means in one direction.

* * * * *